(12) United States Patent
Johnson et al.

(10) Patent No.: US 9,190,853 B2
(45) Date of Patent: Nov. 17, 2015

(54) METHODS AND SYSTEMS FOR ADJUSTING BATTERY VOLTAGE LIMITS

(71) Applicant: GM GLOBAL TECHNOLOGY OPERATIONS LLC, Detroit, MI (US)

(72) Inventors: Kurt M. Johnson, Brighton, MI (US); Robert C. Baraszu, Dearborn, MI (US); Zachary D. Bylsma, Rochester Hills, MI (US); Ashley McAllister, Macomb, MI (US); George Robison, Bloomfield Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 165 days.

(21) Appl. No.: 13/951,246

(22) Filed: Jul. 25, 2013

(65) Prior Publication Data

US 2015/0028814 A1    Jan. 29, 2015

(51) Int. Cl.
*H02J 7/00* (2006.01)
*H02J 7/14* (2006.01)
*H02J 7/04* (2006.01)
*H02J 9/00* (2006.01)
*G01N 27/416* (2006.01)

(52) U.S. Cl.
CPC .............. *H02J 7/00* (2013.01); *G01N 27/416* (2013.01); *H02J 7/04* (2013.01); *H02J 7/14* (2013.01); *H02J 9/00* (2013.01); *Y02T 10/7044* (2013.01); *Y02T 10/7072* (2013.01); *Y02T 10/72* (2013.01)

(58) Field of Classification Search
CPC ................. H02J 7/00; H02J 7/14; H02J 7/04; H02J 9/00; G01N 24/416; B08G 21/00; Y02T 10/7044; Y02T 10/7072; Y02T 10/72

USPC ......... 320/134, 104, 136, 148, 156, 149, 162; 307/156; 324/433, 434; 340/636.12, 340/636.15, 636.17
See application file for complete search history.

(56) References Cited

U.S. PATENT DOCUMENTS

| | | | | |
|---|---|---|---|---|
| 3,927,361 | A * | 12/1975 | Macharg | 320/149 |
| 4,876,513 | A * | 10/1989 | Brilmyer et al. | 324/427 |
| 6,438,487 | B1 * | 8/2002 | Mingo et al. | 701/113 |
| 8,463,564 | B2 * | 6/2013 | Matsumura et al. | 702/63 |
| 9,071,072 | B2 * | 6/2015 | Tamezane | 320/132 |
| 2004/0239333 | A1 * | 12/2004 | Kikuchi | 324/434 |
| 2006/0197536 | A1 * | 9/2006 | Gandhi et al. | 324/426 |
| 2007/0182248 | A1 * | 8/2007 | Blaker et al. | 307/10.1 |
| 2007/0229026 | A1 * | 10/2007 | Morioka et al. | 320/112 |
| 2008/0224671 | A1 * | 9/2008 | Kimura et al. | 322/19 |
| 2009/0218989 | A1 * | 9/2009 | Davis | 320/136 |
| 2009/0315519 | A1 * | 12/2009 | Izumi et al. | 320/134 |
| 2011/0025273 | A1 * | 2/2011 | Lattin | 320/134 |

(Continued)

*Primary Examiner* — Phallaka Kik
(74) *Attorney, Agent, or Firm* — Phillips Ryther & Winchester; Matthew D. Thayne (57) ABSTRACT

Methods and systems for adjusting the voltage limits of a battery. In some implementations, voltage data may be received from each of a plurality of battery sections of a vehicle battery. A voltage offset for the vehicle battery may be calculated using the voltage data. The voltage offset may be calculated by determining a difference between an average voltage taken from each of the plurality of battery sections and at least one of a minimum voltage of all of the battery cells and an average cell voltage from a battery section having the lowest average cell voltage. The voltage offset may be applied to dynamically adjust a voltage limit associated with the vehicle battery so as to prevent any of the battery cells in the vehicle battery from exceeding the voltage limit.

20 Claims, 5 Drawing Sheets

(56) References Cited

U.S. PATENT DOCUMENTS

| | | |
|---|---|---|
| 2011/0109273 A1* | 5/2011 | Tamezane .................... 320/132 |
| 2011/0187325 A1* | 8/2011 | Lin et al. ...................... 320/116 |
| 2011/0309798 A1* | 12/2011 | Hara et al. ................... 320/134 |
| 2012/0019073 A1* | 1/2012 | Huber et al. ................... 307/82 |
| 2012/0187908 A1* | 7/2012 | Tanigawa et al. ............. 320/116 |
| 2013/0038297 A1* | 2/2013 | Sang et al. .................... 320/145 |
| 2013/0257381 A1* | 10/2013 | Diamond et al. ............. 320/134 |
| 2013/0285612 A1* | 10/2013 | Okuda .......................... 320/126 |
| 2013/0335036 A1* | 12/2013 | Zhang et al. .................. 320/162 |
| 2014/0084846 A1* | 3/2014 | Berkowitz et al. ............ 320/107 |
| 2014/0111141 A1* | 4/2014 | Chan et al. ................... 320/107 |

* cited by examiner

METHODS AND SYSTEMS FOR ADJUSTING BATTERY VOLTAGE LIMITS

TECHNICAL FIELD

This disclosure relates to methods and systems for adjusting the voltage limits of a battery, such as a vehicle battery. For example, in some embodiments and implementations, this disclosure relates to methods and systems for dynamically adjusting one or more voltage limits of a high-voltage, electric vehicle battery.

BACKGROUND

Passenger vehicles often include electric batteries for operating features of a vehicle's electrical and drivetrain systems. For example, vehicles commonly include a 12V lead-acid automotive battery configured to supply electric energy to vehicle starter systems (e.g., a starter motor), lighting systems, and/or ignition systems. In electric, fuel cell ("FC"), and/or hybrid vehicles, a high voltage ("HV") battery system may be used to power electric drivetrain components of the vehicle (e.g., electric drive motors and the like).

In certain designs, battery systems included in a vehicle may include one or more sections. For example, a vehicle battery system may include a battery pack that comprises one or more sections of battery cells, such as many current battery systems for electric vehicles, including rechargeable energy storage systems (RESS) for extended-range electric vehicles (EREV). The cells in such batteries may be damaged by overcharging or undercharging such cells.

Many battery systems for electric vehicles therefore include upper and/or lower voltage limits to prevent such cell damage. Such voltage limits, however, are typically static and are applied by utilizing a temperature-based look up table. Moreover, such voltage limits typically do not utilize information about the variation in voltage from cell to cell or section to section.

The present inventors have therefore determined that it would be desirable to provide methods and apparatus for adjusting the voltage limits of a battery, such as an electric vehicle battery, that overcome one or more of the foregoing limitations and/or other limitations of prior art.

SUMMARY

Methods and systems are disclosed herein for adjusting the voltage limits of a battery, such as a vehicle battery for an electric vehicle or hybrid electric vehicle. In some embodiments, the voltage limits of such a battery may be adjusted dynamically, and may incorporate voltage information from multiple cells and/or multiple battery sections of the battery.

In many current vehicle battery systems, voltage limits are calculated as a function of temperature. In some embodiments and implementations of the present invention, an offset may be applied to this preset value. In some such embodiments and implementations, the offset may be applied dynamically such that the offset value changes as voltages within one or more cells and/or battery sections change over time.

In some embodiments and implementations, the offset may be calculated as a difference between a target voltage and an average of the pack. For lower voltage limits, the target voltage may comprise the weakest section average voltage or, alternatively, may comprise the minimum cell voltage in the pack. For upper voltage limits, the target voltage may comprise the weakest section average voltage or the maximum cell voltage in the pack. The offset may be applied to raise a static lower voltage limit, and/or to lower a static upper voltage limit. In some embodiments and implementations, the offset may be configured to increase in magnitude as the difference between the target voltage and an average voltage, such as the average voltage of the pack for example, increases in magnitude. In some embodiments and implementations, the offset may further be configured to decrease in magnitude towards the static limit (in a direction opposite from the previous offset value) based on current throughput.

In this manner, one or more embodiments and/or implementations may be used to more effectively prevent cell over and under voltages. Some embodiments and implementations may further be used to represent limitations of the weakest battery section to the control system, which may be using pack average voltage for control.

In some implementations, a method for dynamically adjusting the voltage limits of a battery may comprise receiving voltage data from at least a plurality of battery cells of a battery. In some implementations, the at least a plurality of battery cells may comprise all of the battery cells of the battery.

A voltage offset for one or more battery voltage limits may be calculated using the voltage data. The voltage offset may be calculated using an average voltage of the at least a plurality of battery cells. In some implementations, the voltage offset may be calculated using a lowest voltage value from the at least a plurality of battery cells. In some implementations, the voltage offset may be calculated using a highest voltage value from the at least a plurality of battery cells.

In some implementations in which the battery comprises a plurality of battery sections, the voltage offset may be calculated using an average voltage of the battery section having the weakest average cell voltage (the weakest battery section). More particularly, in some implementations, the voltage offset may be calculated by calculating the difference between the average voltage of the at least a plurality of battery cells and either a lowest voltage value from the at least a plurality of battery cells or an average voltage of the battery section having the weakest average cell voltage among a plurality of battery sections within the battery. In some implementations, the voltage offset may be calculated by calculating the difference between the average voltage of the at least a plurality of battery cells and either a highest voltage value from the at least a plurality of battery cells or an average voltage of the battery section having the weakest average cell voltage among a plurality of battery sections within the battery.

The voltage offset may be used to adjust a voltage limit associated with the battery to prevent any of the battery cells in the at least a plurality of battery cells from exceeding the voltage limit. The voltage limit may comprise a lower voltage limit or an upper voltage limit. In some implementations, both a lower voltage limit and an upper voltage limit may be dynamically adjusted.

Updated voltage data may then be received from at least a subset of the at least a plurality of battery cells of the battery, after which an updated voltage offset for the battery may be calculated using the updated voltage data. The updated voltage offset may then be applied, after applying the voltage offset, to adjust the voltage limit associated with the battery to prevent any of the battery cells in the at least a plurality of battery cells from exceeding the voltage limit. In this manner, voltage limits may be dynamically updated in accordance with present voltage spreads and, in some embodiments and implementations, may thereby provide for protection based upon the weakest battery section and/or battery cell voltage.

In some implementations, the step of applying a voltage offset may comprise adjusting a static voltage limit by the voltage offset amount. For example, many existing battery systems include a static voltage limit. In some embodiments and implementations of the present invention, this static voltage limit may be dynamically adjusted in accordance with one or more parameters, as discussed elsewhere herein, to provide further protection against over and under charging conditions.

In another example of a method according to one or more principles disclosed herein, the voltage limits of a multi-sectioned vehicle battery may be dynamically adjusted by receiving voltage data from each of a plurality of battery sections of a vehicle battery. The vehicle battery may comprise a plurality of battery cells within each of the plurality of battery sections. A voltage offset for the vehicle battery may be calculated using the voltage data. In some implementations, the voltage offset may be calculated by determining a difference between an average voltage taken from each of the plurality of battery sections and at least one of a minimum voltage of all of the battery cells and an average cell voltage from a battery section having the lowest average cell voltage.

The voltage offset may then be applied to dynamically adjust a lower voltage limit associated with the vehicle battery upwards so as to prevent any of the battery cells in the vehicle battery from exceeding the lower voltage limit.

In some implementations, the voltage offset may be calculated by determining a difference between an average voltage of each of the battery cells of each of the plurality of battery sections and at least one of a minimum voltage of all of the battery cells and an average cell voltage from a battery section having the lowest average cell voltage.

In some implementations, the lower voltage limit may be lowered, after being adjusted upwards and/or an upper voltage limit may be raised, after being adjusted downwards. For example, in implementations and embodiments in which voltage limit adjustments are made to a static voltage limit, the voltage limits may be relaxed towards the static voltage limit. In some implementations, this relaxation of the voltage limit(s) may be performed in response to an indication that at least a subset of the plurality of battery cells is in a charging state. In some such implementations, the amount of relaxation may be correlated with the amount of current throughput.

In an example of an embodiment of a system for dynamically adjusting the voltage limits of a vehicle battery, the system may comprise a vehicle battery comprising a plurality of battery sections. The system may further comprise a voltage sensor configured to sense a voltage from at least one of the plurality of battery sections and a voltage limit adjustment module configured to receive voltage data from the voltage sensor and to calculate a voltage offset using the voltage data. The voltage limit adjustment module may be further configured to apply the voltage offset to adjust a voltage limit associated with the vehicle battery to prevent the vehicle battery from exceeding the voltage limit.

In embodiments in which each of the plurality of battery sections comprises a plurality of battery cells, the voltage limit adjustment module may be configured to prevent any of the battery cells from exceeding the voltage limit. The voltage limit may be a lower voltage limit or an upper voltage limit. In some embodiments, both lower and upper voltage limits may be applied. In some such embodiments, the voltage limit adjustment module may be configured to apply a voltage offset to adjust the upper voltage limit, and may be further configured to apply a voltage offset to adjust the lower voltage limit.

The voltage limit adjustment module may be further configured to apply one or more voltage offsets relative to a static voltage limit. The voltage limit adjustment module may further be configured to adjust the voltage limit towards the static voltage limit during predetermined conditions. The predetermined conditions may comprise an indication that one or more of the cells and/or sections of the vehicle battery are in a charging state. In some such embodiments, the predetermined conditions may comprise a threshold charging current associated with the vehicle battery.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

A detailed description of systems and methods consistent with various embodiments of the present disclosure is provided below. While several embodiments are described, it should be understood that disclosure is not limited to any of the specific embodiments disclosed, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure will be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

Embodiments of the systems and methods disclosed herein may be used to adjust one or more voltage limits associated with a battery. In some embodiments and implementations, such adjustments may be made dynamically, and may be made with respect to a vehicle battery system, such as battery systems in electric, fuel cell, or hybrid vehicles, for example.

Some embodiments disclosed herein may be particularly useful for rechargeable energy storage systems (RESS) within an extended-range electric vehicle (EREV).

Some embodiments may be configured to calculate and/or apply one or more upper voltage limits and/or lower voltage limits that take into account the variation from battery section-to-section and/or cell-to-cell to prevent the section or cell with the lowest/highest voltage from exceeding the voltage limits. In some embodiments, this may be accomplished by dynamically calculating voltage offsets to static voltage limits that can lower the upper limit and/or raise the lower limit in accordance with one or more battery conditions/parameters.

In some embodiments, the voltage offset(s) may be calculated as the difference between a target voltage and the average voltage of the battery pack. For a lower voltage limit, the target voltage may, in some embodiments, be either the average voltage of the weakest battery section or the minimum cell voltage across the whole battery pack. For an upper voltage limit, the target voltage may be either the average voltage of the weakest section or the maximum cell voltage across the whole battery pack. In some embodiments, as discussed in greater detail below, one or more of the voltage offsets may be configured to grow as the difference between target voltage and pack average voltage grows, and may be further configured to decrease back towards the static limits based upon predetermined conditions, such as current throughput.

Some embodiments and implementations may be useful in dealer service refurbishment algorithms that allows for battery section replacement when used with battery packs having sections of non-uniform ages, particularly those embodiments that provide protection based on the weakest section voltage. It is contemplated that other embodiments may be adopted by other, non-refurbishment programs, since some embodiments may alternatively be based upon minimum cell voltages, rather than minimum section voltage.

Figure 1:
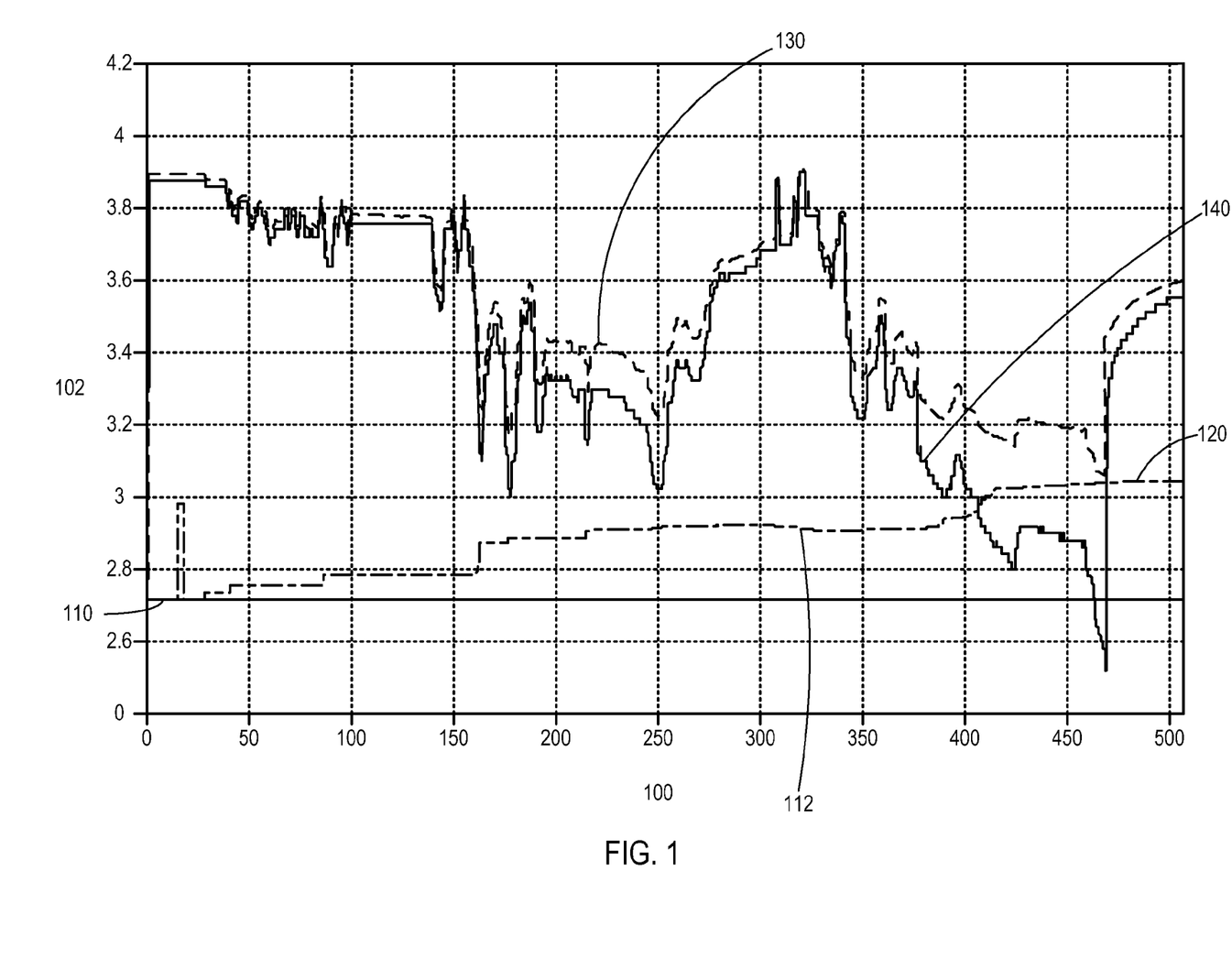
FIG. 1 is a graph illustrating the relationships between various parameters associated with one embodiment of a system for dynamically adjusting a lower voltage limit of a vehicle battery.

Additional details of certain embodiments and implementations will now be discussed in greater detail in connection with the accompanying figures. FIG. 1 depicts a graph illustrating the relationships between various parameters associated with one embodiment of a system for dynamically adjusting a lower voltage limit of a vehicle battery. Time (in seconds) is depicted on the "X" axis at 100 and voltage (in volts) is depicted on the "Y" axis at 102.

A static voltage floor is depicted by line 110. As previously discussed, voltage floor 110 may, in some embodiments, be applied as a function of temperature. However, for purposes of this disclosure, such voltage floors may still be considered "static" because, as discussed in greater detail below, the voltage offsets provided by embodiments of the present invention may be applied, in some embodiments, relative to such a "static" voltage floor. It should be understood that some embodiments may further, or alternatively, comprise a static voltage ceiling.

An adjusted voltage floor is depicted by line 120. The adjusted voltage floor may be calculated by applying a voltage offset to the static voltage floor depicted at 110. FIG. 1 also depicts an average cell voltage of the entire battery pack over time at 130 and an average voltage of the weakest battery section of the pack at 140. The adjusted voltage floor 120 in the depicted embodiment is calculated by applying the difference between lines 130 and 140 to the static voltage floor 110. However, alternative embodiments are contemplated. For example, some embodiments may be configured to calculate and/or apply an adjusted voltage limit as a difference between a minimum cell voltage across the entire battery pack and a pack average voltage.

As depicted in line 120, the adjusted voltage floor rises as the difference between lines 130 and 140 grows. However, some embodiments may also be configured to decrease the adjusted voltage floor during certain predetermined conditions. For example, the graph in FIG. 1 also depicts an adjusted voltage floor 120 that decreases towards static voltage floor 110 at point 112 in response to a charging condition. In some embodiments, the adjusted voltage floor may be configured to lower (in some embodiments towards a static voltage floor) in an amount that correlates with a current throughput associated with the charging condition. Other embodiments may be configured to move towards a static limit by a predetermined amount in response to any indication of current throughput.

For example, in some embodiments, a 10% change in state of charge may result in a return from a dynamic voltage limit to a static limit. As such, for a 45 Ahr capacity battery pack, for instance, a net charge current (charge current−discharge current) of 4.5 A over a 1 hour time period may result in a relaxation of the dynamic limit back to the static limit. In some embodiments, the relaxation towards the static limit may take place in multiple discrete iterations. For example, in some embodiments, each increase (or reduction) of 2% in state of charge may result in a 20% relaxation of the voltage limit towards a static limit (20% of the difference between the dynamic and static limit).

In some embodiments, voltage relaxation towards a static floor (or ceiling) may be, for example, configured to tie the amount of voltage relaxation to the amount of charge added (or removed from) one or more cells and/or sections of the battery. For example, each 1%, 3%, or 5% added or subtracted from a state of charge may result in a corresponding, predetermined reduction or increase in the voltage limit.

Figure 2:
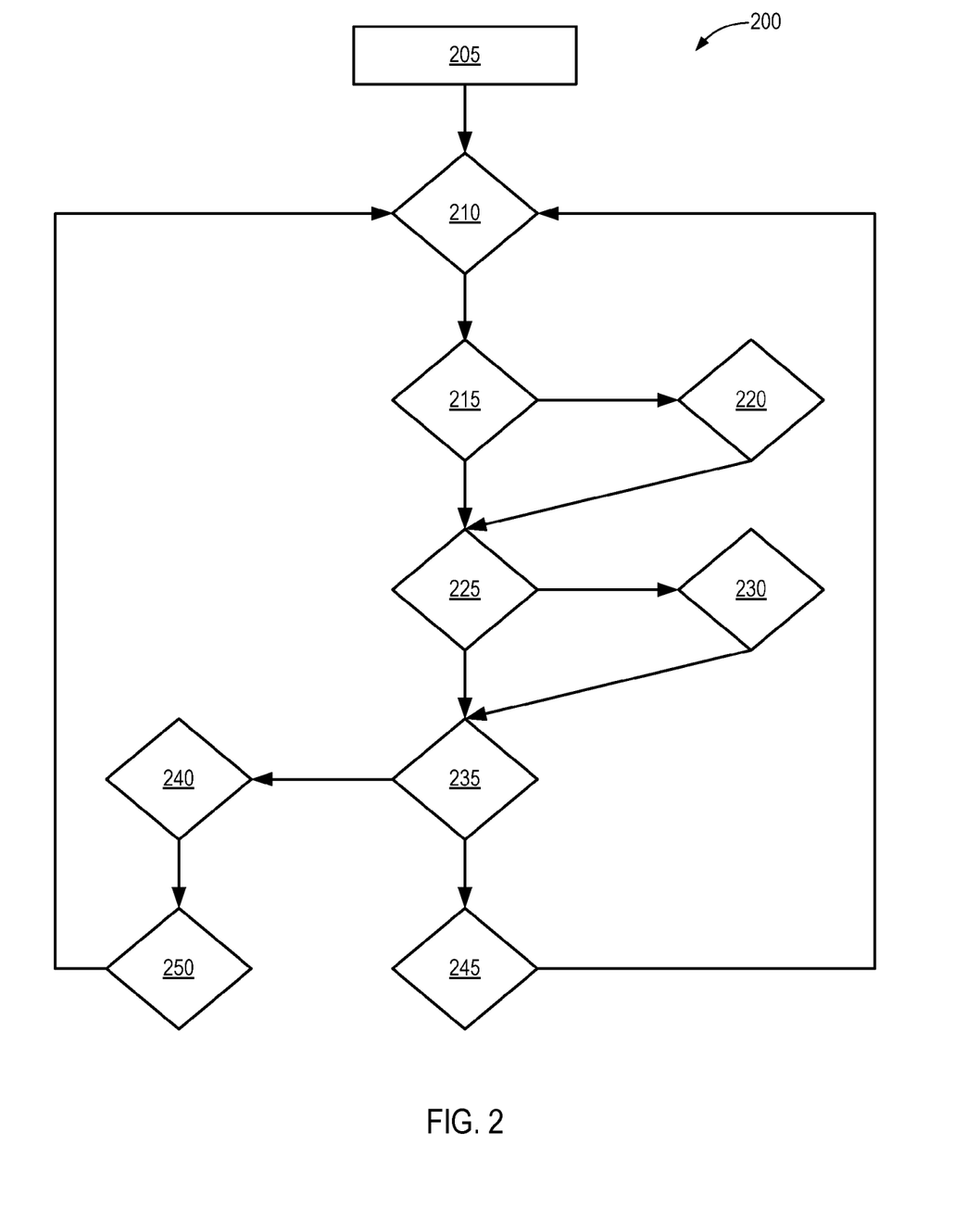
FIG. 2 is a flow chart illustrating an example of a method for adjusting battery voltage limits.

FIG. 2 is a flow chart illustrating an example of a method 200 for adjusting battery voltage limits. Method 200 may begin at step 205, wherein a static voltage limit may be applied. In some implementations, step 205 may comprise applying a static voltage floor. In other implementations, step 205 may comprise applying a static voltage ceiling. In still other implementations, step 205 may comprise applying both a static voltage floor and a static voltage ceiling. In some implementations, the static voltage limit may be configured to vary as a function of temperature. However, for purposes of this disclosure, such voltage limits should still be considered "static" since they do not vary in accordance with voltage readings associated with the battery.

Following step 205, a voltage offset may be calculated at step 210. The voltage offset may be calculated as the difference between a first dynamically-sensed voltage and a second dynamically-sensed voltage associated with a battery. Preferably, the first dynamically-sensed voltage comprises a voltage that provides an assessment of an overall voltage of the battery and the second dynamically-sensed voltage comprises a voltage that provides an assessment of a low-end voltage of the pack, such as a voltage of a weakest cell in the pack or a voltage of a weakest section in the pack.

For example, in some implementations, the first dynamically-sensed voltage may comprise an average voltage across the entire vehicle battery pack and the second dynamically-sensed voltage may comprise a target voltage. The target voltage may comprise an average voltage of the weakest battery section and/or the battery section having the lowest overall voltage. Alternatively, the target voltage may comprise a minimum cell voltage across the entire pack.

The calculated voltage offset may be compared with a previous offset value, if any, at step 215. If the previous offset value is less that the voltage offset, process 200 may proceed to step 220 at which the new voltage offset may be updated. In some implementations, the new voltage offset may be updated relative to a static voltage limit, such as a static voltage floor. In other implementations, the new voltage offset may be updated relative to a previous voltage offset value, if any. In some implementations, step 220 may only be configured to update the new voltage offset if the voltage offset differs from a previous voltage offset by a predetermined amount, so as to avoid having the dynamic voltage limit(s) vary continuously with each variation between the two dynamically-sensed voltages, irrespective of how small. However, in other embodiments and implementations, the dynamic voltage limit(s) may vary continuously as the offset values change.

If, at step 215, the previous offset value is greater than the calculated voltage offset, the process may proceed from step 215 directly to step 225. Alternatively, if the previous offset value is less that the calculated voltage offset, process 200 may proceed to step 225 from step 220 after the new voltage offset has been updated. Step 225 may comprise determining whether a voltage associated with one or more cells and/or sections of the battery has increased and/or sensing whether a current is flowing into (or out of) one or more of the cells and/or sections to charge/discharge those cells/sections.

For example, in some implementations, step 225 may comprise seeking an indication of whether at least a subset of the plurality of battery cells is in a charging state. In embodiments configured to alter an upper voltage limit, step 225 may comprise detecting a discharging current of at least a threshold amount. In some implementations, step 225 may comprise detecting a particular current. For example, step 225 may comprise detecting a charging current of at least a threshold amount. In other implementations, step 225 may comprise detecting a charging current of any amount.

In response to an indication that at least a subset of the plurality of battery cells is in a charging state, process 200 may proceed to step 230, at which a relaxation voltage limit adjustment may be made. In implementations in which the voltage limit is a lower voltage limit, for example, step 230 may comprise lowering the voltage limit. In implementations in which the voltage limit is a lower voltage limit and in which a static voltage limit is employed, step 230 may comprise lowering/relaxing the lower voltage limit towards the static limit. In some implementations, step 230 may comprise adjusting the voltage limit in an amount that correlates with a current throughput associated with the charging state. In some embodiments, the current throughput may be calculated by timing a constant charging current.

If no charging current is detected, an insufficient charging current is detected, or otherwise an indication is received that at least a subset of the plurality of battery cells is not in a charging state, process 200 may proceed from step 225 to step 235, at which point a determination may be made as to whether the updated offset is greater than a predetermined maximum offset value. Process 200 may alternatively proceed to step 235 from step 230, as indicated in FIG. 2, if an indication is received that at least a subset of the plurality of battery cells is in a charging state.

If the calculated offset value is greater than the maximum offset value, then process 200 may then proceed to step 240, at which point the offset voltage is set as the maximum offset value. Following step 240, the voltage limit may be applied at step 250 as the maximum voltage offset value plus any static voltage limit.

If, on the other hand, the calculated offset value is less than the maximum offset value, then the voltage limit may be applied at step 245 as the calculated offset value plus any static voltage limit value. Either from step 245 or step 250, process 200 may then return to step 210, at which point an updated voltage offset may be calculated and the process may repeat to dynamically and continuously update the voltage offset in accordance with updated voltage data/readings from the battery.

A simplified implementation of the process depicted in FIG. 2 is represented below. Initially, a static voltage floor (VoltFloor) may be set as a function of temperature. Then, a voltage offset (DeltaVolt) may be calculated as, for example, an average voltage of the battery pack (PackAvgVoltage) minus a target voltage (TargetVoltage). TargetVoltage may be, for example, either the weakest section average voltage (which may be most useful for refurbished battery packs and/or packs with non-uniform sections) or the minimum cell voltage in the pack.

An updated voltage limit may then be applied as follows. If DeltaVolt(k)>a previous offset value (Offset(k−1)), then the updated voltage offset (Offset(k)) may be set as Offset(k)=RateLimit(DeltaVolt(k)−Offset(k−1))+Offset(k−1)). If a charging current is detected (in some implementations, a predetermined charging current), then the updated voltage limit may be set as Offset(k)=(max(DeltaVolt(k), Offset(k−1))−(Offset(k−1)−DeltaVolt(k))*CurrentAdjFactor(k))−Offset(k−1))+Offset(k−1). The CurrentAdjFactor(k) may be applied, for example, as follows:

$$\text{CurrentAdjFactor}(k) = \text{Current}(k)/(36000 * \text{Capacity}) * (\text{SOC Recover \%})$$

As such, where 36000=(3600 sec/hour)/0.1 sec (sample time), Capacity=45 Ahr, and SOC Recover %=10%, CurrentAdjFactor(k)=Current(k)/((36000*45)*0.1))=162,000. Thus, for example, supposing Current(k)=4.5 A, over one hour, the SOC would increase by about 10%.

If DeltaVolt(k)<Offset(k−1), then the updated voltage offset, Offset(k), may be left alone—i.e., Offset(k)=Offset(k−1). As discussed above, in some implementations, a comparison may also be made to ensure that the voltage limit does not exceed a maximum voltage offset (MaxOffset). In other words, if Offset(k)>MaxOffset, then Offset(k)=MaxOffset. The updated voltage limit may then be calculated and/or applied as the static voltage limit, VoltFloor, if any, plus Offset(k).

Figure 3:
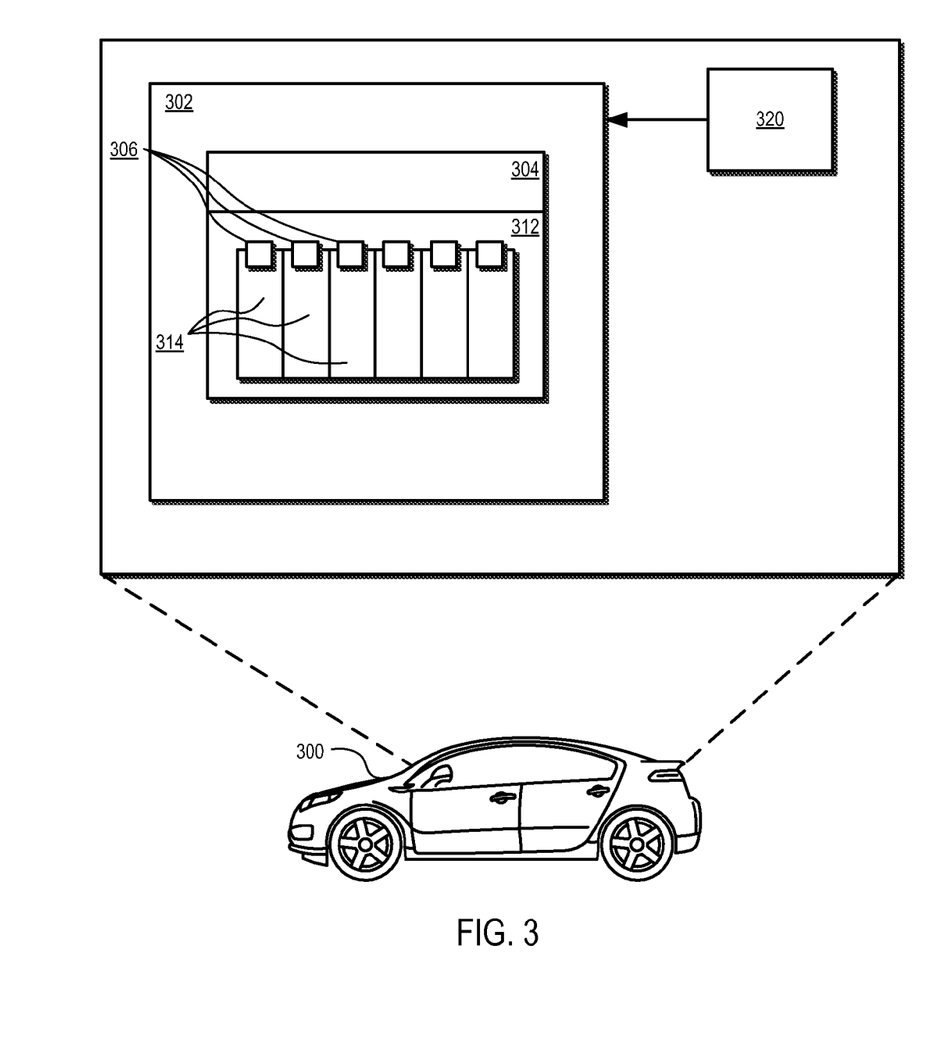
FIG. 3 illustrates a vehicle comprising one embodiment of a system for adjusting a voltage limit of a vehicle battery.

FIG. 3 illustrates a vehicle 300 comprising one embodiment of a system for adjusting a voltage limit of a vehicle battery. Vehicle 300 may be a motor vehicle, a marine vehicle, an aircraft, and/or any other type of vehicle, and may include an internal combustion engine ("ICE") drivetrain, an electric motor drivetrain, a hybrid engine drivetrain, a FC drivetrain, and/or any other type of drivetrain suitable for incorporating the systems and methods disclosed herein. Vehicle 300 may comprise a battery system 302. Battery system 302 may be used to power electric drivetrain components (e.g., as in an electric, hybrid, or FC power system). In some embodiments, battery system 302 may be configured to supply electric energy to a variety of vehicle systems, including, for example, vehicle starter systems (e.g., a starter motor), lighting systems, ignition systems, and/or the like.

Battery system 302 may comprise battery electronics 304. Battery electronics 304 may be configured to monitor and control certain operations of battery system 302. For example, battery electronics 304 may be configured to monitor and control charging, discharging, and/or balancing operations of battery system 302. In certain embodiments, battery electronics 304 may be communicatively coupled with one or more sensors (e.g., sensors 306), actuation devices (e.g., electrical relays), communication devices and/or systems configured to enable the battery electronics 304 to monitor and control operations of the battery system 302.

Battery system 302 may include one or more battery packs 312 suitably sized and configured to provide electrical power to the vehicle 300. Each battery pack 312 may include one or more battery sections 314. The battery sections 314 may comprise one or more battery cells utilizing any suitable battery technology including, for example, lead-acid, nickel-metal hydride ("NiMH"), lithium-ion ("Li-Ion"), Li-Ion polymer, lithium-air, nickel-cadmium ("NiCad"), valve-regulated lead-acid ("VRLA") including absorbed glass mat ("AGM"), nickel-zinc ("NiZn"), molten salt (e.g., a ZEBRA battery), and/or other suitable battery technologies. Sensors 306 may comprise voltage sensors configured to sense a voltage from one or more of the battery sections 314.

Vehicle 300 may also comprise a voltage limit adjustment module 320. Voltage limit adjustment module may be configured to receive voltage data from one or more voltage sensors 306 and may be further configured to calculate a voltage offset using the voltage data. Voltage limit adjustment module 320 may be further configured to apply the voltage offset to adjust a voltage limit associated with battery system 302 to prevent the vehicle battery from exceeding the voltage limit.

Voltage limit adjustment module 320 may comprise any type of computer instruction or computer executable code located within a memory device and/or m-readable storage medium. Voltage limit adjustment module 320 may, for example, comprise one or more physical or logical blocks of computer instructions, which may be organized as a routine, program, object, component, data structure, etc., that performs one or more tasks or implements particular abstract data types.

In certain embodiments, voltage limit adjustment module 320 may comprise disparate instructions stored in different locations of a memory device, which together implement the described functionality of the module. Indeed, a module may comprise a single instruction or many instructions, and may be distributed over several different code segments, among different programs, and across several memory devices. In addition, data, such as voltage data, may be resident in the same memory device, or across several memory devices, and may be linked together in fields of a record in a database across a network.

In some embodiments, voltage limit adjustment module 320 may be configured to prevent any of the battery cells in the vehicle from exceeding the voltage limit. The voltage limit applied by voltage limit adjustment module 320 may comprise a lower voltage limit or an upper voltage limit. In some embodiments, voltage limit adjustment module 320 may be configured to calculate and/or apply both a lower and an upper voltage limit.

The voltage limit adjustment module 320 may be configured to apply a voltage offset relative to a static voltage limit such that the voltage limit comprises a voltage offset relative to the static voltage limit. Voltage limit adjustment module 320 may be further configured to adjust the voltage limit towards the static voltage limit during predetermined conditions. In some embodiments, the predetermined conditions may comprise a threshold charging current associated with the vehicle battery system 302.

The battery electronics 304 may further be configured to provide information to and/or receive information from other systems included in the vehicle 300. For example, the battery electronics 304 may be communicatively coupled with voltage limit adjustment module 320, as indicated in FIG. 3. In other embodiments, voltage limit adjustment module 320 may be a part of battery electronics 304. In still other embodiments, voltage limit adjustment module 320 may be executed on a remote computer or computers at one site and coupled to the vehicle 300 via a communication network, or may be distributed across multiple sites and interconnected by a communication network.

Some embodiments and implementations may be configured to implement separate methods for dynamically adjusting an upper voltage limit and for dynamically adjusting a lower voltage limit. Thus, FIGS. 4 and 5 illustrate examples of implementations of methods for dynamically adjusting lower voltage limits and upper voltage limits, respectively.

Figure 4:
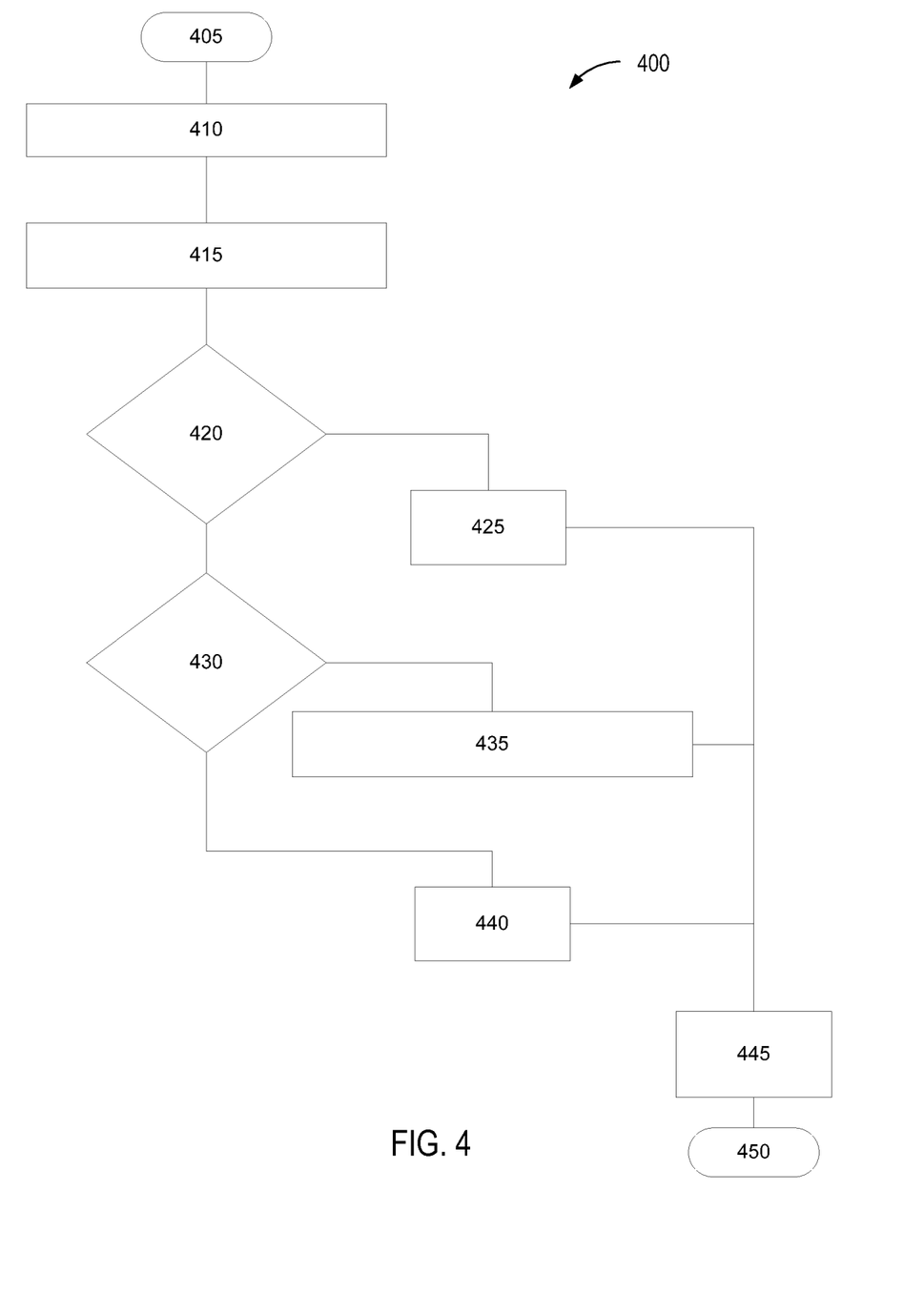
FIG. 4 is a flow chart illustrating an example of a method for dynamically adjusting a lower voltage limit of a vehicle battery.
Figure 5:
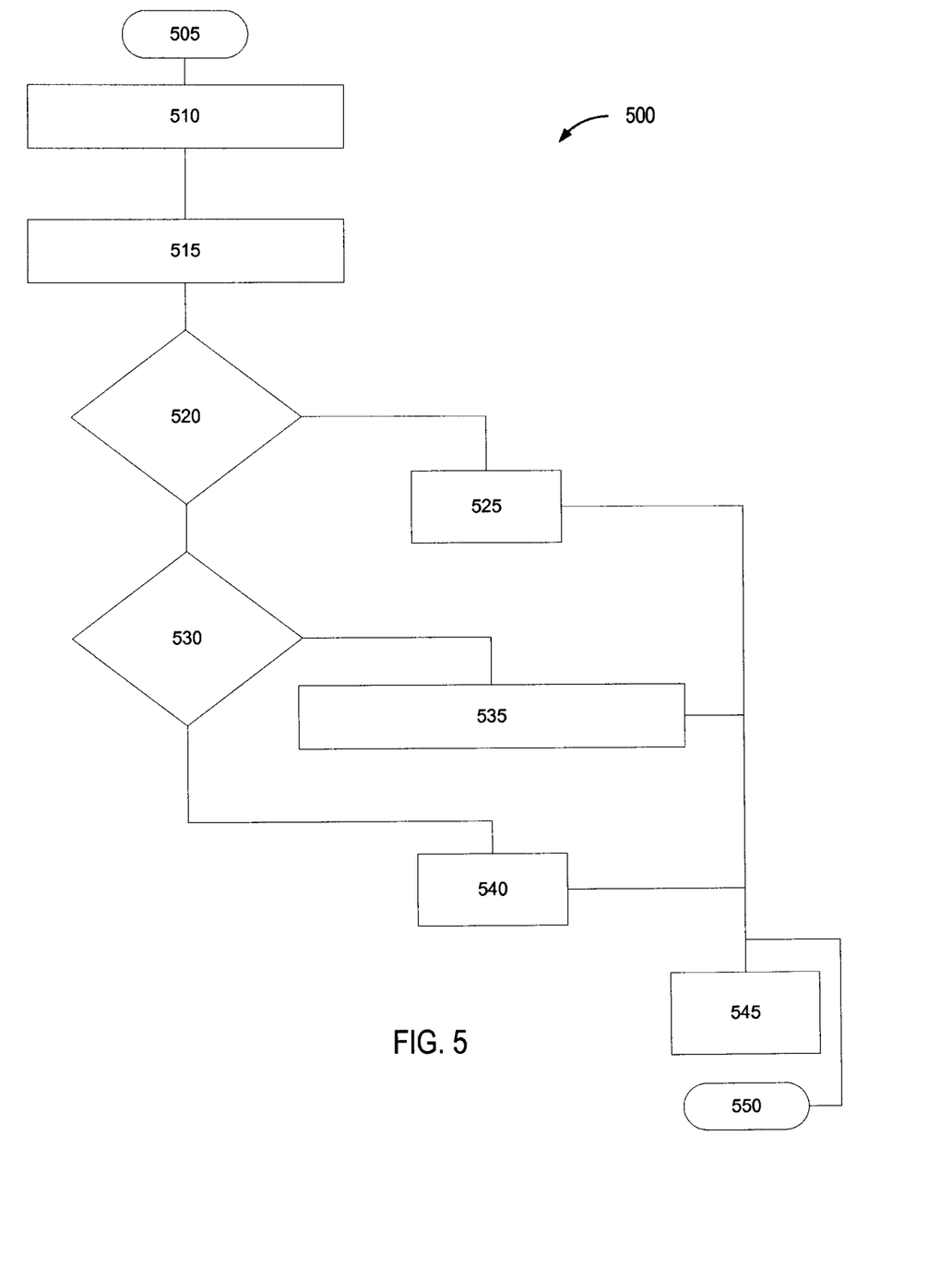
FIG. 5 is a flow chart illustrating an example of a method for dynamically adjusting an upper voltage limit of a vehicle battery.

FIG. 4 begins at step 405, at which the method 400 may begin. At step 410, a lower limit offset, if any, may be stored as the "last offset." If there are no previous lower limit offsets, the lower limit offset may be stored as zero. This may provide a comparison to history in later steps.

After the previous offset is stored as the last offset, method 400 may proceed to step 415, at which point the difference between an average voltage of all cells (or at least a subset of all cells) in the battery and an average or minimum voltage of "target cells" may be calculated. The "target cells" may be, for example, the cells in a section defined as "weak" in a pack of sections having non-uniform age or the minimum cell voltage of a particular section or the entire battery pack.

Step 420 may then executed as an IF/ELSEIF/ELSE function. More particularly, if the present difference between the average voltage and the target cell voltage is greater than or equal to the last offset, then the present offset may be set to the present difference at step 425.

If the present difference between the average voltage and the target cell voltage is less than the last offset, method 400 may proceed to step 430. Step 430 may comprise detecting whether the battery current is charging. In some implementations, step 430 may comprise detecting a threshold amount of battery charging. If the battery current is charging, or sufficiently charging, the process may proceed to step 435, at which point the present offset may be calculated and set as a value that is between the last offset and the present difference. How much the present offset is moved from the last difference may be dependent on the magnitude of the detected current, the estimated battery capacity, and/or a calibratable value that represents the amount of state of charge movement to "recover" from the historical event (SOC_R).

In some implementations, this calculation may be made using the following equation:

$$\text{MAX}\left[\left(\text{Last Offset} - \dfrac{(LastOffset - \text{Present Difference}) * \left(\dfrac{\text{Current}}{Capacity * \dfrac{3600}{dt}}\right)}{SOC_R}\right), PresentDifference\right]$$

In such implementations, the max function may be used in this equation because the values are positive (including current). When SOC_R is a large number, a large current is needed to subtract a substantial value from the last offset. This situation would hold more history for a longer period of time, given a current.

If no current, or an insufficient current and/or change in state of charge is detected at step 430, no change may be made to the offset from the previous offset. In other words, the offset may be set as the previous offset at step 440.

In some implementations, the present offset may be gradient limited. In other words, in such implementations, not more than a threshold amount of movement from the last offset may be allowed in either direction.

Absolute limits and/or gradient limits may be applied at step 445, if needed, to adjust the offset. In some implementations, the offset may be limited so as to never be less than zero or greater than a calibration. For a cell level this might be, for example, a maximum of 1 volt.

The final offset value may then be added to a static lower limit at 450. Since the offset is positive, it will raise the lower limit.

An example of an implementation for dynamically adjusting an upper voltage limit is shown in FIG. 5 at 500. In some implementations in which a vehicle also uses a method for dynamically adjusting a lower voltage limit, the variable names used may be different in the software code in order to avoid sharing of data between upper and lower limit calculation, except where the input signals are the same.

Process 500 begins at step 505. At step 510, the upper limit offset may be set as the "last offset." This may provide a comparison to history in later steps. At step 520, the difference between an average of all cells, or at least a subset of all cells, and the average of a set of target cells may be calculated. In some implementations, the target cells may be the cells in a section defined as "weak" in a pack of sections having non-uniform age. Alternatively, the target cells may be the cells having a maximum voltage of a particular section or a maximum voltage of all cells in the entire battery pack.

Process 500 may then proceed to as an IF/ELSEIF/ELSE function. If the difference at the present time step is less than the previous time step's offset, then the present offset may be set to the present difference at step 525. In the upper limit calculation of the process depicted in FIG. 5, these values will be negative numbers.

Step 530 may comprise detecting whether the battery current is discharging. In some implementations, step 530 may comprise detecting a threshold amount of battery discharging. If the battery current is discharging (current<0), or sufficiently charging, the process may proceed to step 535, at which point the present offset may calculated as a value that is between the last offset and the present difference. How much the present offset moves from the last difference may, in some implementations, depend on the magnitude of the current, the estimated battery capacity, and/or a calibratable value that may represent the amount of state of charge movement to "recover" from a historical event (SOC_R). In some implementations, this value (SOC_R) may be distinct from the corresponding SOC_R value used in connection with a lower voltage limit adjustment process, such as process 400.

In some implementations, this calculation may be made using the following equation:

$$\text{MIN}\begin{bmatrix} PresentDifference, \\ \left( \text{Last Offset} + (LastOffset - \text{Present Difference}) * \left( \dfrac{Current}{\dfrac{Capacity * \dfrac{3600}{dt}}{SOC_R}} \right) \right) \end{bmatrix}$$

The MIN function may be used here because the values are negative (including current). Use of this function will therefore result in the largest negative number being selected.

If neither of the two conditions associated with steps 520 and 530 are met, no change is made to the offset from the previous offset. In other words, the offset may be set as the last offset at step 540.

In some implementations, the present offset may be gradient limited. In other words, only a certain amount of movement from the last offset may be allowed in either direction. Some implementations may be further, or alternatively, be configured to apply absolute limits. Thus, for example, in some implementations the offset may be configured so as to never exceed zero and/or be less than a calibration level threshold. For a cell level this might be, for example, a minimum of −1 volt. Any absolute and/or gradient limits may be applied to the offset at step 545, after which the final offset value may be added and/or applied to the static upper limit at step 550. Since the offset is negative, it will lower the upper voltage limit.

In some embodiments and implementations, one or more of these calculations may be performed on the scale of cell voltages and scaled to pack level voltages for use in a vehicle battery control system. Such algorithms may be used to account for cell to cell or section to section variation in the upper and lower voltage limits of the battery pack when pack voltage is used for control.

The foregoing specification has been described with reference to various embodiments. However, one of ordinary skill in the art will appreciate that various modifications and changes can be made without departing from the scope of the present disclosure. For example, various operational steps, as well as components for carrying out operational steps, may be implemented in alternate ways depending upon the particular application or in consideration of any number of cost functions associated with the operation of the system. Accordingly, any one or more of the steps may be deleted, modified, or combined with other steps. Further, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced, are not to be construed as a critical, a required, or an essential feature or element.

Those having skill in the art will appreciate that many changes may be made to the details of the above-described embodiments without departing from the underlying principles of the invention. The scope of the present invention should, therefore, be determined only by the following claims.

The invention claimed is:

1. A method for dynamically adjusting voltage limits of a battery, the method comprising the steps of:
    receiving voltage data from at least a plurality of battery cells of a battery;
    calculating a voltage offset for the battery using the voltage data;
    applying the voltage offset to adjust a voltage limit associated with the battery to prevent any of the battery cells in the at least a plurality of battery cells from exceeding the voltage limit;
    receiving updated voltage data from at least a subset of the at least a plurality of battery cells of the battery;
    calculating an updated voltage offset for the battery using the updated voltage data, wherein the updated voltage offset is calculated using a difference between the average voltage of the at least a plurality of battery cells and one of a lowest voltage value from the at least a plurality of battery cells and an average voltage of a battery section having the weakest average cell voltage among a plurality of battery sections within the battery; and applying the updated voltage offset after applying the voltage offset to adjust the voltage limit associated with the battery to prevent any of the battery cells in the at least a plurality of battery cells from exceeding the voltage limit.

2. The method of claim 1, wherein the at least a plurality of battery cells comprises all of the battery cells of the battery.

3. The method of claim 1, wherein the voltage limit comprises a lower voltage limit.

4. The method of claim 1, wherein the voltage offset is calculated using an average voltage of the at least a plurality of battery cells.

5. The method of claim 4, wherein the voltage offset is calculated using a lowest voltage value from the at least a plurality of battery cells.

6. The method of claim 4, wherein the battery comprises a plurality of battery sections, and wherein the voltage offset is calculated using an average voltage of the battery section having the weakest average cell voltage.

7. The method of claim 4, wherein the voltage offset is calculated by calculating a difference between the average voltage of the at least a plurality of battery cells and one of a lowest voltage value from the at least a plurality of battery cells and an average voltage of the battery section having a weakest average cell voltage among a plurality of battery sections within the battery.

8. The method of claim 1, wherein the step of applying the voltage offset comprises adjusting a static voltage limit by an amount of the voltage offset.

9. A method for dynamically adjusting voltage limits of a multi-sectioned vehicle battery, the method comprising the steps of:
receiving voltage data from each of a plurality of battery sections of a vehicle battery, wherein the vehicle battery comprises a plurality of battery cells within each of the plurality of battery sections;
calculating a voltage offset for the vehicle battery using the voltage data, wherein the voltage offset is calculated by determining a difference between an average voltage taken from each of the plurality of battery sections and at least one of a minimum voltage of all of the battery cells and an average cell voltage from a battery section having the lowest average cell voltage; and
applying the voltage offset to dynamically adjust a lower voltage limit associated with the vehicle battery upwards, wherein the lower voltage limit is configured to prevent any of the battery cells in the vehicle battery from exceeding the lower voltage limit.

10. The method of claim 9, wherein the voltage offset is calculated by determining a difference between an average voltage of each of the battery cells of each of the plurality of battery sections and at least one of a minimum voltage of all of the battery cells and an average cell voltage from a battery section having the lowest average cell voltage.

11. The method of claim 9, further comprising lowering the lower voltage limit.

12. The method of claim 11, wherein the step of lowering the lower voltage limit is performed in response to an indication that at least a subset of the plurality of battery cells is in a charging state.

13. The method of claim 12, wherein the step of lowering the lower voltage limit comprises lowering the voltage limit in an amount that correlates with a current throughput associated with the charging state.

14. A system for dynamically adjusting voltage limits of a vehicle battery, comprising:
a vehicle battery comprising a plurality of battery sections;
a voltage sensor configured to sense a voltage from at least one of the plurality of battery sections; and
a voltage limit adjustment module configured to receive voltage data from the voltage sensor and configured to calculate a voltage offset using the voltage data, wherein the voltage limit adjustment module is configured to calculate the voltage offset using a difference between at least two dynamic voltage values, wherein the voltage limit adjustment module is further configured to apply the voltage offset to adjust a voltage limit associated with the vehicle battery to prevent the vehicle battery from exceeding the voltage limit.

15. The system of claim 14, wherein each of the plurality of battery sections comprises a plurality of battery cells, and wherein the voltage limit adjustment module is configured to prevent any of the battery cells from exceeding the voltage limit.

16. The system of claim 14, wherein the voltage limit comprises a lower voltage limit.

17. The system of claim 14, wherein the voltage limit adjustment module is configured to apply a voltage offset to adjust an upper voltage limit, and wherein the voltage limit adjustment module is further configured to apply a voltage offset to adjust a lower voltage limit.

18. The system of claim 14, wherein the voltage limit adjustment module is configured to apply the voltage offset relative to a static voltage limit, and wherein the vehicle battery is configured so as to avoid exceeding the static voltage limit.

19. The system of claim 18, wherein the voltage limit adjustment module is configured to adjust the voltage limit towards the static voltage limit during predetermined conditions.

20. The system of claim 19, wherein the predetermined conditions comprise a threshold charging current associated with the vehicle battery.

* * * * *